(12) United States Patent  
Nicholls et al.

(10) Patent No.: US 9,795,333 B2  
(45) Date of Patent: Oct. 24, 2017

(54) BLOOD SAMPLING DEVICES

(75) Inventors: Clive Nicholls, Buckinghamshire (GB); Christopher Hudson, Oxfordshire (GB)

(73) Assignee: OWEN MUMFORD LIMITED, Oxford (GB)

( * ) Notice: Subject to any disclaimer, the term of this patent is extended or adjusted under 35 U.S.C. 154(b) by 509 days.

(21) Appl. No.: 13/978,280

(22) PCT Filed: Jan. 6, 2012

(86) PCT No.: PCT/GB2012/050026  
§ 371 (c)(1),  
(2), (4) Date: Sep. 25, 2013

(87) PCT Pub. No.: WO2012/093268  
PCT Pub. Date: Jul. 12, 2012

(65) Prior Publication Data  
US 2014/0052024 A1    Feb. 20, 2014

(30) Foreign Application Priority Data  
Jan. 7, 2011    (GB) .................................. 1100222.7

(51) Int. Cl.  
*A61B 5/151*    (2006.01)  
*A61B 5/15*    (2006.01)

(52) U.S. Cl.  
CPC .... *A61B 5/15111* (2013.01); *A61B 5/150022* (2013.01); *A61B 5/15113* (2013.01);  
(Continued)

(58) Field of Classification Search  
CPC .......... A61B 5/15111; A61B 5/150618; A61B 5/15117; A61B 5/150297; A61B 5/1411;  
(Continued)

(56) References Cited

U.S. PATENT DOCUMENTS 5,137,521 A    8/1992    Wilkins  
5,324,302 A    6/1994    Crouse  
(Continued)

FOREIGN PATENT DOCUMENTS

CN    1265870 A    9/2000  
CN    1525837 A    9/2004  
(Continued)

OTHER PUBLICATIONS

International Search Report, dated Apr. 4, 2012, from corresponding PCT application.

(Continued)

*Primary Examiner* — David J McCrosky  
(74) *Attorney, Agent, or Firm* — Young & Thompson

(57) ABSTRACT

A blood sampling device includes a housing and a lancet supporting a lancet needle or tip, the lancet and needle being urged or urgeable in a pricking direction. A trigger mechanism is moveable to a fire position for releasing the lancet to travel in the pricking direction. A removable safety cap initially covers the lancet needle. The lancet has an initial position in which movement of the trigger mechanism to the fire position is blocked and an intermediate position in which the trigger mechanism may be moved to the fire position. The intermediate position is obtainable only on removal of the safety cap.

10 Claims, 2 Drawing Sheets

(52) U.S. Cl.
CPC ...... *A61B 5/15117* (2013.01); *A61B 5/15142* (2013.01); *A61B 5/150297* (2013.01); *A61B 5/150412* (2013.01); *A61B 5/150503* (2013.01); *A61B 5/150549* (2013.01); *A61B 5/150618* (2013.01); *A61B 5/150625* (2013.01); *A61B 5/150717* (2013.01)

(58) Field of Classification Search
CPC .......... A61B 5/15142; A61B 5/150022; A61B 5/15113; A61B 5/150549; A61B 5/150717; A61B 5/15058–5/150625
See application file for complete search history.

(56) References Cited

U.S. PATENT DOCUMENTS

| | | | |
|---|---|---|---|
| 5,741,288 A | | 4/1998 | Rife |
| 2003/0130597 A1 | | 7/2003 | Marshall |
| 2007/0162063 A1 | | 7/2007 | Marshall et al. |
| 2009/0275860 A1* | | 11/2009 | Nakamura ......... A61B 5/15142 600/573 |

FOREIGN PATENT DOCUMENTS

| | | |
|---|---|---|
| CN | 101912268 A | 12/2010 |
| EP | 0 293 092 A2 | 11/1988 |
| EP | 1 690 562 A1 | 8/2006 |
| GB | 2 451 840 A | 2/2009 |
| JP | 2005/342325 A | 12/2005 |
| WO | 93/19671 A1 | 10/1993 |
| WO | 02/065910 A1 | 8/2002 |
| WO | 2004/080305 A1 | 9/2004 |
| WO | 2005/013825 A1 | 2/2005 |
| WO | 2006/109452 A1 | 10/2006 |
| WO | 2007/050528 A1 | 5/2007 |
| WO | 2009/081130 A1 | 7/2009 |
| WO | 2009/095701 A1 | 8/2009 |

OTHER PUBLICATIONS

GB Search Report, dated May 10, 2011, from corresponds to GB application.

* cited by examiner

BLOOD SAMPLING DEVICES

BACKGROUND OF THE INVENTION

Field of the Invention

This invention relates to blood sampling devices of the type which employs a sharp tip or needle to obtain a small sample of blood for testing purposes.

Description of the Related Art

Known blood sampling devices employ a spring or the like which forces a needle tip into the skin following triggering of the device. Embodiments of this invention are concerned with improving the safety of such devices to reduce the risk of accidental triggering where a manually actuated trigger is employed. In addition it is known from eg our own earlier WO2005/013825 to provide a needle cap which is removable prior to use of the device. However, in some instances, if a user does not follow the written and visual instructions to twist the cap off they may force the cap off in a way that causes the device to malfunction.

WO2007/050528 discloses a single use lancing device having a removable cap that prevents the lancet from being moved to a puncture position 15 before the cap is removed. After removal of the cap the device is fired by depressing a firing button which pushes the lancet forward to force protrusions on the lancet past cantilevered heads on the housing thereafter to be driven forwards.

BRIEF SUMMARY OF THE INVENTION

According to one aspect, the invention provides a blood sampling device comprising:

a housing;

a lancet body having associated therewith a sharp tip, the lancet body being urged or urgeable forwardly in a pricking direction;

a trigger mechanism moveable to a fire position for releasing the lancet body to travel in the pricking direction; and a removable safety cap for at least partially covering the lancet tip; wherein the lancet has an initial position in which movement of the trigger mechanism to its fire position is blocked and an intermediate position in which the trigger mechanism may be moved to its fire position, said intermediate position being obtainable upon removal of the safety cap.

Thus, the device cannot be triggered until the cap is removed, and this reduces the risk of accidentally activating the trigger mechanism prior to removal of the cap.

The firing mechanism may take many forms; it may comprise a manually operable firing button or the like. This is conveniently located on the side of the device so that the device is fired by applying pressure in a direction transverse to the pressure direction but other orientations are possible such as on the rear of the device.

Preferably the trigger mechanism comprises a trigger member movable from a rest position, in which it restrains movement of said lancet body, to said fire position in which said restraint is removed. Preferably said trigger member is mounted to move generally transversely to the forward path of the movement of the lancet body. Preferably said trigger member is mounted for rocking movement relating to said housing. The rocking movement may be about an axis transverse to the forward path of the movement of the lancet body.

In an embodiment, the cap is removable in the pricking direction and when removed allows the lancet body to be urged in the pricking direction by a spring into the intermediate position ready for further urging by the spring when the trigger mechanism is operated to release the lancet body for forward movement from the intermediate position.

In an embodiment, the lancet includes an abutment surface engageable in blocking alignment with an abutment surface of the trigger mechanism to prevent movement of the trigger mechanism into the fire position when the lancet is in said initial position.

Conveniently, the abutment surface on the lancet is moveable with the lancet to the intermediate position when the cap is removed, whereupon the respective abutment surfaces are no longer in blocking alignment, and thereby movement of the trigger mechanism into its fire position is possible.

Preferably the intermediate position is maintained by the engagement of a pawl of the trigger mechanism with a latch surface of the lancet. The lancet body may support a lancet needle which provides said sharp tip or the tip may be integrally formed therewith.

Conveniently the trigger mechanism includes a tiltable trigger lever having a hinge region between the trigger abutment surface and the pawl, and said engagement of the trigger abutment surface and the lancet abutment surface prevents or limits hinging of the trigger lever.

Preferably, the spring is in the form of a compression spring which acts on the housing and the lancet to provide said urging.

Conveniently, the cap has a graspable portion external to the housing and a stem substantially within the housing.

Preferably, said stem includes one or more projections which extend in a plane perpendicular and/or transversely to the pricking direction, and the housing includes a complementarily shaped aperture, the cap being captured by the stem projections in the aperture, but being releasable from said aperture upon twisting said cap to cause the or each projection and the complementarily shaped aperture to be in substantial alignment.

In an embodiment the projections include a pair of opposed barbs on either side of the stem and the aperture is in the form of a slot which allows the forward passage of the barbs in one orientation of the barbs but prevents their forward passage in other orientations.

According to another aspect the invention provides a blood sampling device comprising:

a housing having an aperture in a forward end thereof:

a lancet body with an associated sharp tip located within said housing;

a cap having a stem portion which covers the needle and extends forwardly through said aperture to merge with an externally accessible tab portion;

a locking arrangement for restraining forward movement of said cap and being twistably releaseable from a locked position to a released position, wherein said locking arrangement comprises respective abutments on said stem portion and said housing, which are aligned to block forward movement of the cap when it is in the locked position but which allow forward movement from a pre-firing to an armed position when the cap is twisted to its free position, and at least one of the locking abutments is resiliently moveable to allow it to be snapped rearwardly past the cooperating abutment during assembly.

In this manner the abutments may be disposed within the housing and inaccessible from outside thereby reducing the opportunity for forcible release.

Conveniently said locking abutment on said housing comprises a wall of an aperture through which the stem may pass on release. The slot may be a transverse slot of elongate form, and the locking abutment on said stem conveniently comprises two oppositely directed transverse projections from said stem. Advantageously the stem is provided with two resiliently moveable abutments. Conveniently the or each abutment is of barbed form, and ideally integrally formed on a slotted portion of said stem, thereby to provide resilience.

According to another aspect, this invention provides a method of producing a blood sampling device which includes:

providing a housing having an aperture in a forward end thereof and moveable from an open position to a closed position during assembly, providing a lancet body having an associated sharp tip and including an integrally formed cap comprising a stem which at least partially covers the tip and extends forwardly to merge with an externally accessible tab, the stem having at least one abutment that cooperates in use with an abutment on the housing, locating the lancet body with its integrally formed cap and the device spring in the housing when open, with the spring in a relatively relaxed state and the tab spaced forwardly of the housing, closing the housing, and thereafter effecting relative movement of the cap rearwardly with respect to the housing to compress the drive spring and to snap the or each abutment past the abutment in the housing to retain the lancet in a firing or pre-firing position by engagement of said abutments.

In yet another aspect this invention provides a blood sampling device comprising:

a housing;

a lancet body having a sharp tip and being urged or urgeable forwardly in a pricking direction, and a manually operable trigger member movable to a fire position for releasing the lancet to travel in the pricking direction, wherein the lancet has:

an initial position in which movement of the trigger member to its fire position is blocked by an abutment surface on the lancet body being in blocking alignment with a complementary abutment surface on said trigger member, and an intermediate position spaced forwardly of the initial position in which the abutment surfaces are shifted out of alignment so that the trigger mechanism may be moved to its fire position.

The invention extends to any single feature or combination of the features mentioned herein or illustrated in the drawings.

BRIEF DESCRIPTION OF THE DRAWINGS

The invention may be put into effect in various ways, and one embodiment will now be described below, by way of example only, with reference to the drawings wherein.

DETAILED DESCRIPTION OF THE PREFERRED EMBODIMENTS

Figure 1:
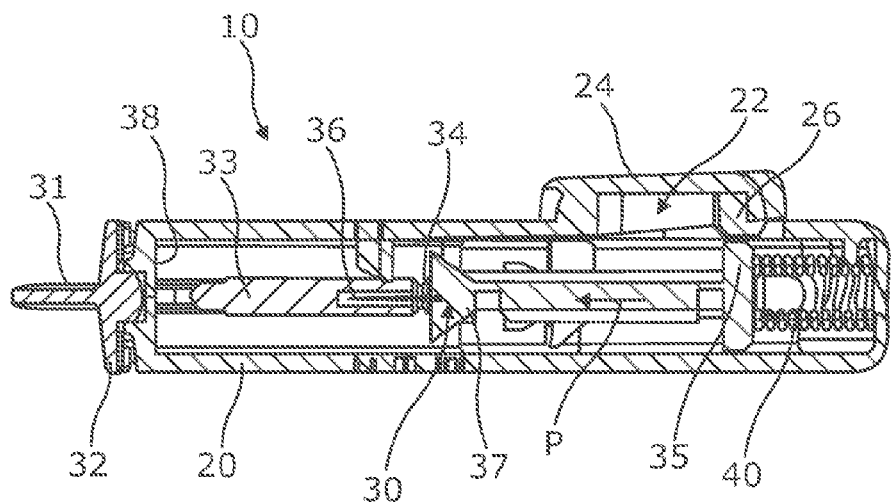
FIG. 1 shows a longitudinal section through a blood sampling device.
Figure 2:
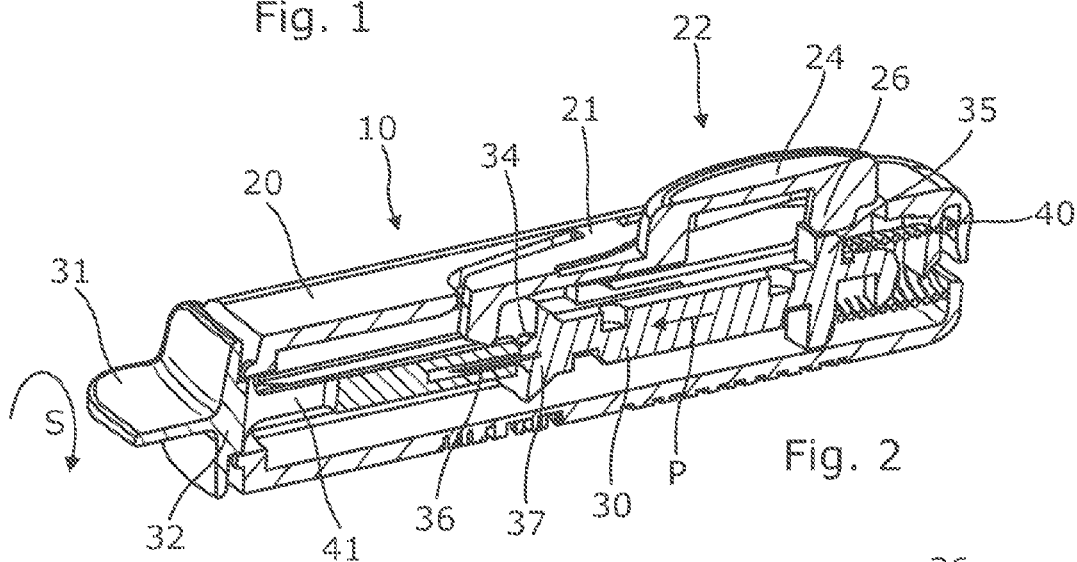
FIG. 2 shows the section shown in FIG. 1, as a perspective view.

Referring to FIGS. 1 and 2, the main components of the blood sampling device 10 are a housing 20, a lancet 30 movable within the housing 20, and a coil spring 40 for causing pricking movement. The housing 20 includes a trigger mechanism 22, and the lancet includes an integrally moulded safety cap 32 which covers a lancet needle 36. The cap 32 comprises an externally accessible tab connected to the remainder of the lancet 30 by means of a stem 33 which has a frangible connection 34 at the interface with the lancet.

The housing 20 is formed from moulded plastics in two hinged halves. During assembly, the lancet 30 and spring 40 are located substantially within the two halves of the housing 20 in the arrangement shown in FIG. 1, with the spring 40 in its relaxed position. To complete the assembly, the safety cap is pushed back into the housing where it latches thereby compressing the spring 40 and so urging the lancet 30 in a pricking direction shown by arrow P. The lancet 30 is prevented from moving in the housing 20 because the safety cap 32 interlocks with an end face 38 of the housing 20 and restrains the lancet 30 from movement. This is the initial, as assembled, condition of the device 10 with the lancet held in a pre-firing position, back from an armed position.

The trigger mechanism 22 includes a push button 24 which hinges about two transverse live hinges 21 that connect it to the housing. The button has a lower rib 26 which is engageable with a boss 35 formed on the lancet 30. In the initial position shown, the boss prevents depression of the trigger button 24 and so prevents operation of the trigger mechanism.

Figure 3:
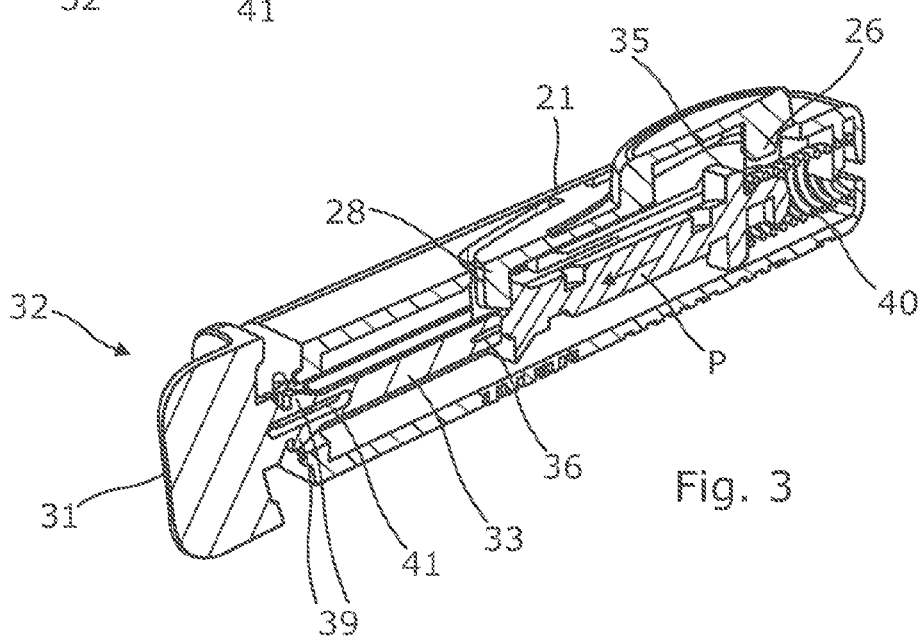
FIG. 3 is a perspective view similar to FIG. 2, with the cap twisted through 90° and the lancet shifted forwardly into engagement with the trigger.

The safety cap 32 has a graspable tab 31 which in use is held and twisted by 90° in the direction of arrow S, i.e. about the direction of pricking, in order to remove it (FIG. 3). The cap 32 is then freeable from the housing 20 in a manner described below. The twisting action breaks the frangible connection 34 and withdrawal of the cap 32 in the direction of arrow P exposes the skin pricking needle 36 inside the housing 20. Thus, until this time the needle is hermetically sealed prior to use.

The removal of the cap 32 also simultaneously allows the lancet 30 to move forward in the direction of arrow P, into an intermediate position in which a detent 37 on the lancet 30 abuts a pawl 28 of the trigger mechanism 22. In this position, the push button 24 is no longer prevented from being depressed because the boss 35 has moved forward out of the path of the rib 26. Thus the device is armed and ready for use once the cap has been fully withdrawn in the direction of arrow P.

Once the cap 32 has been removed, the device is ready to be fired, by holding the proximal end against the skin, and depressing the trigger button 24. That action lifts the pawl 28 about the live hinges 21. In turn the detent 37 is set free and the spring 40 forces the lancet 30 in the direction of arrow P, so that the needle 36 protrudes from the proximal end of the housing 20, to puncture the skin, and thereafter rebound so that the tip is returned safely within the housing but with the lancet well forward of the cocked position.

Figure 4:
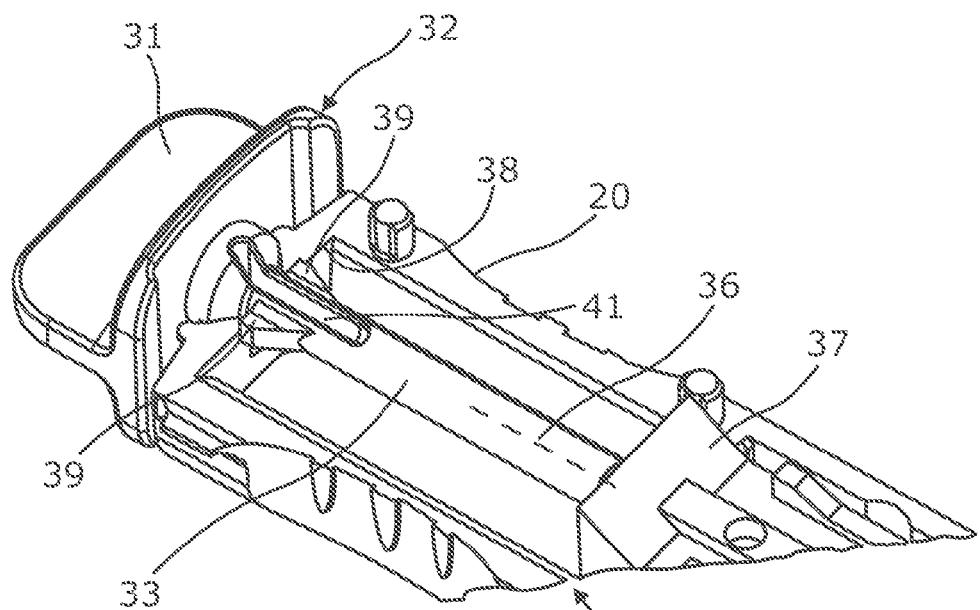
FIG. 4 shows an enlarged sectional partial view of the device shown in FIG. 1 showing the cap attachment.

FIG. 4 shows an enlarged view of the proximal end of the device with one half of the housing removed for clarity. The lancet 30, as mentioned above, includes a removable safety cap 32 which is initially held in place by an interlocking arrangement with the housing. Two sprung barbs 39 are formed on the stem 33 of the cap 32 and abut the end 38 of the housing 20 to prevent movement of the cap under the influence of spring 40. The barbs 39 are sprung by provision of a slot 41. When the cap 32 is twisted through 90 degrees, the frangible connection 34 connecting the valve 33 of the cap 32 to the lancet 30 is broken, and the barbs 39 align with a complementary slot 29 (FIG. 6) in the housing 20 and the cap is pushed partially out of the housing by the drive spring until the lancet reaches the intermediate position mentioned above. Thereafter the stem 33 of the cap 32 can be pulled out of the housing 20 via the aperture 29.

The profile of the barbs 39, the resilience afforded by the slot 41, and the dimensions of the slot 29 are selected so that during assembly, having located the integrally formed lancet 30 and cap 32 in the housing together with the spring 40 in a relaxed extended condition, the assembly may be completed by pushing the cap into the body until the barbs 39 snap past the slot 29 thereby cocking the spring 40, and locking the cap and lancet in the initial position against forward movement until the cap is released by twisting.

Figure 5:
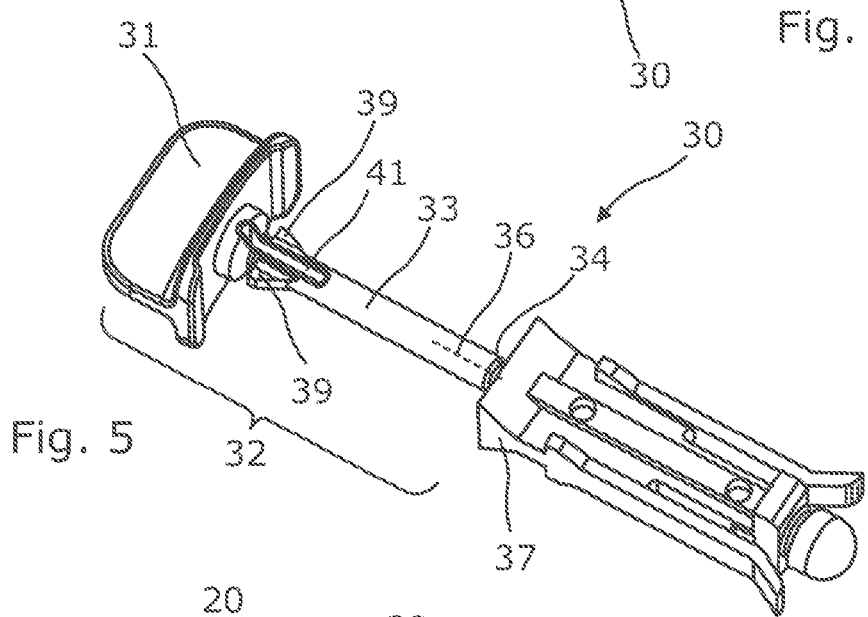
FIG. 5 shows the integral cap and lancet 8 of the device shown in FIG. 1.

FIG. 5 shows the integral plastics moulding of the lancet 30 and the cap 32. The frangible connection 34 connecting the cap 32 to the remainder of the lancet 30 is visible.

Figure 6:
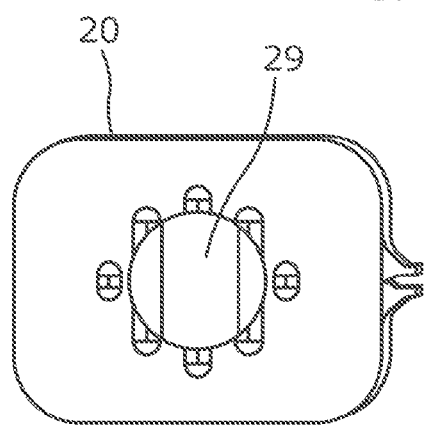
FIG. 6 is a view of one end of the device.

FIG. 6 shows the slot 29 which allows the cap to escape once it is twisted, and when the barbs 39 and slot 29 are in alignment.

The invention claimed is:

1. A blood sampling device comprising:
a housing (20);
a lancet body (30) movable within the housing (20), the lancet body (30) having an end that includes a sharp tip (36), the lancet body (30) having an initial pre-firing position, an intermediate armed position, and a final fired position with the sharp tip (36), after having protruded from a proximal end of the housing (20), is rebounded within the housing with the lancet body (30) forward of the intermediate armed position;
an urging mechanism (40) that urges the lancet body and the sharp tip (36) to move, within the housing, forwardly in a pricking direction from the initial pre-firing position, to the intermediate armed position, and then to the final fired position;
a trigger mechanism (22) comprised of a trigger member (24) moveable from an initial rest position to a fire position where the trigger mechanism releases the lancet body (30) from the intermediate armed position to travel in the pricking direction to the final fired position, wherein,
i) with the lancet body (30) in the initial pre-firing position, the trigger member (24) is engaged with an element (35) of the lancet body (30) such that the element (35) of the lancet body blocks movement of the trigger member (24) from the rest position to the fire position thereby restraining movement of the trigger member (24) and preventing operation of the trigger mechanism, and
ii) with the lancet body (30) in the intermediate armed position, the trigger member (24) is no longer engaged with the element (35) of the lancet body (30) and operation of the trigger member (24) moves the trigger member (24) from the initial rest position to the fire position where the trigger mechanism (22) releases the lancet body (30) from the intermediate armed position to have the urging mechanism move the lancet body (30) and the sharp tip (36) forwardly in the pricking direction to the final fired position; and
a removable safety cap (32) that at least partially covers the sharp tip (36), the safety cap (32) being at least partially located within the housing (20), the safety cap (32) holding the lancet body (30) in the initial pre-firing position and restraining the lancet body (30) from moving, within the housing, in the pricking direction, wherein removal of the safety cap (32) exposes the sharp tip (36) and allows the urging mechanism (40) to move the lancet body (30) from the initial pre-firing position to the intermediate armed position where the device is armed and ready for use by operation of the trigger member (24),
wherein the lancet body (30) can only move into said intermediate armed position when the safety cap has been removed,
wherein the intermediate armed position of the lancet body (30) is maintained by engagement of a pawl (28) of the trigger mechanism (22) with a latch surface (37) of the lancet body, and operation of the trigger member (24) moving into the fire position lifts the pawl (28) from the latch surface (37) thereby allowing the urging mechanism (40) to move the lancet body (30) and the sharp tip (36) with the sharp tip (36) protruding from the proximal end of the housing (20), and
wherein the trigger member (24) is comprised of a push button (24) hinged about a hinge region (21), the push button including a part (26) that engages with a boss (35) on the lancet body (30), said engagement of the part (26) with the boss (35) on the lancet body (30) limiting movement of the push button (24) from the initial rest position.

2. A device according to claim 1, wherein said trigger member (24) is mounted to move generally transversely to a forward path of the movement of the lancet body (30) in the pricking direction.

3. A device according to claim 2, wherein said trigger member (24) is mounted for rocking movement relating to said housing (29).

4. A device according to claim 1, wherein,
the urging mechanism (40) includes a drive spring (40), the cap (32) is removable in the pricking direction and, when removed, allows the lancet body (30) to be urged in the pricking direction by the drive spring (40) into the intermediate armed position ready for further urging by the drive spring when the trigger mechanism (22) is operated.

5. A device according to claim 4, wherein said drive spring (40) comprises a compression spring.

6. A device according to claim 1, wherein the element (35) of the lancet body (30) is a first abutment surface (35) that, when the lancet body (30) is in said initial pre-firing position, engages with a second abutment surface (26) of the trigger member (24) to prevent movement of the trigger member (24) from the initial rest position into the fire position.

7. A device according to claim 6, wherein, when the cap (32) is removed, the first abutment surface (35) on the lancet body (30) moves with the lancet body (30) from the initial pre-firing position to the intermediate armed position, whereupon the respective first and second abutment surfaces (35, 26) are no longer engageable and movement of the trigger member (24) into the fire position is possible.

8. A device according to claim 1, wherein the cap (32) has
i) an externally graspable portion (31) external to the housing,
ii) a stem (33) substantially within the housing, the stem at least partially covering the sharp tip and extending forwardly to merge with the externally graspable portion (31), and
iii) a frangible connection (34) that connects the stem to the end of the lancet body (30).

9. A device according to claim 8, wherein,
said stem (33) includes one or more projections (39) which extend in a plane perpendicular to the pricking direction,
the housing (20) includes an aperture (29) complementarily shaped to the one or more projections (39), and
the cap (32) is captured in the aperture by each projection (39) abutting the housing, but releasable from said aperture (29) upon twisting the cap to align each projection (39) with the aperture (29).

10. A device according to claim 9, wherein each projection includes a pair of opposed barbs (39) on either side of the stem (33) and the aperture is in the form of a slot (29) which allows a forward passage of the barbs through the slot in one orientation of the barbs but prevents the forward passage of the barbs through the slot in other orientations.

* * * * *